(12) United States Patent
Scherr

(10) Patent No.: US 7,128,929 B1
(45) Date of Patent: *Oct. 31, 2006

(54) ALGINATE FOAM COMPOSITIONS

(76) Inventor: George H. Scherr, P.O. Box 134, Park Forest, IL (US) 60466

( * ) Notice: Subject to any disclaimer, the term of this patent is extended or adjusted under 35 U.S.C. 154(b) by 60 days.

This patent is subject to a terminal disclaimer.

(21) Appl. No.: 09/676,670

(22) Filed: Oct. 2, 2000

Related U.S. Application Data

(63) Continuation-in-part of application No. 09/301,228, filed on Apr. 29, 1999, now abandoned.

(30) Foreign Application Priority Data

Oct. 13, 1999  (GB) .................................... 9924266

(51) Int. Cl.
*A61F 13/00* (2006.01)
*A16K 9/00* (2006.01)

(52) U.S. Cl. ...................... 424/443; 424/444; 424/445; 424/446; 424/447; 424/448; 424/400; 424/401; 424/414; 424/415; 424/416; 424/417; 604/304

(58) Field of Classification Search ........ 424/400–401, 424/404–407, 414–417, 430–437, 443–449; 604/304; 602/41, 42, 59
See application file for complete search history.

(56) References Cited

U.S. PATENT DOCUMENTS

| | | | | | |
|---|---|---|---|---|---|
| 3,948,881 | A | * | 4/1976 | Strong | 260/209.6 |
| 5,089,606 | A | * | 2/1992 | Cole et al. | 536/54 |
| 5,470,576 | A | * | 11/1995 | Patel | 424/445 |
| 5,674,524 | A | * | 10/1997 | Scherr | 424/445 |
| 5,676,964 | A | * | 10/1997 | Della Valle et al. | 424/423 |
| 5,851,461 | A | * | 12/1998 | Bakis et al. | 264/50 |
| 5,998,692 | A | * | 12/1999 | Gilding | 602/41 |
| 6,696,077 | B1 | * | 2/2004 | Scherr | 424/443 |

FOREIGN PATENT DOCUMENTS

JP          09119023          *  5/1997

OTHER PUBLICATIONS

Deroyal wound care product and Multidex treatment system package information, 1999.*
US 5,778,916, Feb. 1998, Scherr (withdrawn).*

* cited by examiner

*Primary Examiner*—Sreeni Padmanabhan
*Assistant Examiner*—Shahnam Sharareh
(74) *Attorney, Agent, or Firm*—Ladas & Parry LLP

(57) ABSTRACT

The specification discloses an alginate foam composition dressing which may be prepared with or without a backing. The foam dressing exhibits unique capability in including soluble or insoluble medicaments as part of the alginate foam composition, attributes not inherent in alginate dressings prepared by spinning. The dressings so prepared also eliminate the need for adhesives and secondary dressings for retaining an alginate dressing on a wound site.

33 Claims, No Drawings

ALGINATE FOAM COMPOSITIONS

This application is a continuation-in-part of U.S. patent application Ser. No. 09/301,228, filed Apr. 29, 1999, now abandoned.

DESCRIPTION OF THE PRIOR ART

U.S. Pat. No. 5,718,916 issued to Scherr describes in some detail the background of the use of alginates as well as their application in medical and veterinary medicine; said outline of the background data for the use of alginates as set forth in U.S. Pat. No. 5,718,916 in columns 1, 2, and column 3 to line 33, are incorporated herein by reference.

ATTRIBUTES OF THE INVENTION DESCRIBED HEREIN

The U.S. Pat. No. 5,718,916 more specifically deals with the preparation of a sponge-like or foam alginate composition which requires lyophilization or freeze drying in order to remove the aqueous component of the composition and so results in a foam product which has certain advantages over fiber-related alginates which are produced by a spinning process.

An advantage of the invention described herein relates to the preparation of foam alginate compositions in which the aqueous portion of the composition can be removed by air-drying or regulated heat drying without the necessity of utilizing an expensive freeze-drying apparatus so significantly reducing the cost of the final product as well as the reduction in time of its preparation.

In the U.S. Pat. No. 5,718,916 for the preparation of alginate foam products, note that the examples cited and many of the claims made, utilize a sequestering agent such as sodium citrate in order to delay the immediate precipitation of calcium alginate when calcium salts are add d to a solution of sodium alginate. Since the sequestering agent does not permit too long an extended period of time prior to the alginate being precipitated as the calcium salt, the examples cited in U.S. Pat. No. 5,718,916 clearly indicate that the composition has to be added to a dish or tray immediately after mixing prior to its being frozen and lyophilized.

It is thus another salient advantage of the invention described herein, that no sequestering agent is required and that the calcium alginate so formed permits a semi-solid gel to be poured into any receptacle even hours after it is formed without the restraints of having to immediately place it into a dish prior to its being dried by a suitable method.

The lack of a restraint of the element of time in preparing the calcium foam alginate composition as described herein makes feasible the adjustment of viscosity of the composition without the necessity to work quickly and freeze the mixture as is made necessary in U.S. Pat. No. 5,718,916, prior to its being dried and prepared for use in medical or veterinary applications. Where it might be necessary to effect an adjustment of pH in the alginate foam composition, the operator can also make such adjustments over the period of time necessary without the restraint of time that is inherent in the U.S. Pat. No. 5,718,916.

It is generally known in the profession that sodium alginate in aqueous solution is highly sensitive to precipitation by calcium ions and that even as low a concentration of 1 to 100,000 of sodium alginate in aqueous solution, can result in precipitation of calcium alginate in the presence of such solutions as calcium chloride. Since the calcium alginate foam composition prepared herein is highly viscous and would result in a viscosity that may be difficult to layer in a homogenous thin layer on a plate to permit its drying, it was discovered that the addition of ammonia in aqueous solution or ammonium salts would reduce the viscosity of the calcium alginate foam composition and significantly improve the ease with which the layering of the calcium alginate foam composition may be layered. Since, during the drying process, free ammonia is liberated from such a composition which has included the use of a solution of ammonia, liberation of the ammonia will then result in enhanced viscosity and concomitantly increase strengthening of the foam composition thus prepared by the removal of ammonia during the drying process.

The use of various dressings frequently require that they be very soft and amenable to being draped around fingers, arms, or legs where injury has occurred. Consequently, it is a desirable attribute of such dressings to be highly flexible and amenable to being easily draped without their surface being distorted by the stress of such draping. It has been discovered that the addition of a compound such as sodium tetraborate (borax) results in the calcium alginate foam composition to become highly flexible, have an increased elasticity, and can be readily draped around small circumferences such as a finger without distortion or breakage of the alginate dressing so formed.

Another salient advantage of the invention described herein concerns the feasibility of adding ingredients to the alginate composition, which ingredients may contain properties such as being particulate, having high viscosity, or having or resulting in a rheology which is undesirable in making it feasible for such compositions to be forced through a fine spinneret to produce the alginate fibers as currently practiced in the profession.

The use of desirable particulate matter such as microparticles that can act as time-release particles, aqueous insoluble medicaments, or even the use of intact cells such as yeast cells, blood cells, or human or animal tissue cells, that might be desirable to apply to an open wound may be introduced into the alginate foam composition described herein. As is well known in the profession the pH of the alginate composition may have to be adjusted to be commensurate with the cells that are to be incorporated in the final composition, and such pH adjustment is readily made by those skilled in the art. Such particulate matter and/or aqueous insoluble matter which can be incorporated into the alginate foam composition described in our patent is an attribute not feasible when calcium alginate fibers are prepared by a spinning process.

U.S. Pat. Nos. 4,778,679 and 5,177,065 deal with the treatment of wounds utilizing a starch hydrolyzate (a maltodextrin). Example 1 in U.S. Pat. No. 4,778,679 utilizes a starch hydrolyzate powder blended with approximately 5% ascorbic acid which is merely sprinkled as a powder onto an open wound or ulcer site which then must be covered with a dressing. Example 3 in U.S. Pat. No. 4,778,679 also describes the use of such a maltodextrin, to which has been added sodium ascorbate, but again it is applied by sprinkling the powder onto an open wound or lesion. Example 6 in U.S. Pat. No. 4,778,679 sprinkles a starch hydrolyzate to which has been added 5% ascorbic acid and a solution of multiple amino acids. U.S. Pat. No. 5,177,065 teaches the use of a starch hydrolyzate (maltodextrin) powder which is applied to an open wound and which ultimately hardens to form a hardened surface in and on the wound or lesion. In the same patent, U.S. Pat. No. 5,177,065 the authors find a need to increase the adherence of the starch hydrolyzate powder composition (claim 2) by adding other products to it, which might assist it in forming an adhesion to the wound in the form of a film, such as the use of various film forming agents.

A typical application of the teachings of U.S. Pat. Nos. 4,778,679 and 5,177,065 can be gleaned from the use of a maltodextrin wound dressing called Multidex,® which is manufactured by DeRoyal Industries, Inc. Said Multidex product is provided for the treatment of wounds in the form of a powder which is sprinkled on the wound and which then requires an appropriate dressing to hold the powder in place. DeRoyal Industries, Inc. also supplies maltodextrin wound dressing in the form of a gel which is squeezed from a foil packet onto a wound, but still requires a secondary dressing (the DeRoyal literature describing the Multidex Maltodextrin brand wound dressings are contained in their clinical reprint #1076-2213).

Neither U.S. Pat. Nos. 5,177,065 and 4,778,679, nor anyone in the profession has succeeded in preparing a dressing which in and of itself will contain the starch hydrolyzate (maltodextrin) compositions described in the patents U.S. Pat. Nos. 5,177,065 and 4,778,679 and in the commercial products of DeRoyal which can be packaged, sterilized, stored, and used directly on a wound at any appropriate time that is desired without the need to use a multiplicity of products and the awkward use of powders and ointments, which then require an additional dressing as described in the above literature. The alginate foam composition described herein serve as a unique matrix for a maltodextrin component.

Having set forth the tenets of the invention contained herein, the following non-limiting examples illustrate various compositions that are inherent in our invention.

DESCRIPTION OF THE PREFERRED EMBODIMENTS

EXAMPLE 1

Place 4000 ml of deionized water into a plastic container and, with stirring, slowly add 100 grams of Kelco HV brand of sodium alginate. The stirring should be sufficiently vigorous to form a vortex in the water so that the sodium alginate added to the water is directed into the middle of the vortex to ensure a very efficient dispersion of the alginate particles and so increase the rate of solution. The mixture is stirred until all of the sodium alginate has been dissolved.

To 1125 ml of the 2.5% sodium alginate solution prepared as above, add the following ingredients:

---

15 grams of sodium bicarbonate (Na $HCO_3$),
75 ml of glycerin,
6.9 ml of the surface active agent polyoxyethylene - polyoxypropylene block polymer (L64, Wyandotte Corp.)
6.9 ml of the surface active agent polyoxyethylenesorbitan monooleate (Tween 80 ®, Atlas Chemical Industries, Inc.)

---

After stirring vigorously for approximately ten minutes to ensure that all of the ingredients have been dispersed, add 100 ml of deionized water containing 45 grams of sodium tetraborate ($Na_2B_4O_7.10H_2O$). After stirring for a few minutes to ensure that the borate solution has been thoroughly dispersed, add 33 ml of ammonium hydroxide (28% $NH_3$) and 15 grams of polyethylene glycol (average MN CA 1000).

While continuously stirring, slowly add 9 grams of calcium sulfate ($CaSO_4.2H_2O$) into the vortex of the alginate solution and then follow with 35 ml of a dilute solution of acetic acid prepared by diluting one part of glacial acetic acid with 2 parts of deionized water.

The diluted acetic acid should be added very slowly with a pipette, again into the vortex of the stirred mixture, and vigorous stirring continued for approximately five minutes.

Following the addition of the acetic acid, the composition will gradually become more viscous. One should now add 1800 ml of deionized water.

The alginate composition thus prepared will contain a considerable amount of foam, which foam will not rise to the surface of the alginate composition, because the viscosity of the final alginate composition is greater than the buoyancy of the foam. When poured onto a plate, such as one made of plastic or metal, the dish may be air-dried or placed into a drying oven on the following schedule of drying:

---

70° C. - 2 hours
60° C. - 2 hours
40° C. - until dry

---

Alternately, the alginate composition prepared as above can be poured onto a backing composed of a cotton-rayon mixture or a polyester non-woven backing, so that an amount of the alginate foam mixture penetrates into the fiber and thus when dry, will retain this backing as part of the dried finished dressing.

The U.S. Pat. No. 5,674,524 expressed novelty in that prior to said U.S. patent, the manufacturers of alginate fiber dressings were obliged to recommend that, once the alginate fiber dressing is placed on a wound, then a secondary sterile dressing would have to be affixed on top of the alginate dressing prior to its being affixed in place with adhesive tapes. The U.S. Pat. No. 5,674,524 resolved the laborious and expensive procedure for alginate dressings to require two separate sterile dressings to be affixed over a wound. This was resolved by utilization of needle punching of the alginate fiber dressing to a backing following the carding operation. It is a unique attribute of the patent described herein, that even needle punching is unnecessary to have the foam alginate composition affixed to a suitable backing of an alginate dressing.

It is thus another salient advantage of the patent described herein that the dried alginate foam composition, when ready to be cut into appropriate sized dressings, packaged, and sterilized ready for use, already has a backing affixed to the alginate foam composition and does not require any additional secondary sterile backing after the alginate composition is placed on an open wound.

EXAMPLE 2

Add 1200 ml of the 2.5% sodium alginate HV brand as prepared above in Example 1 to a 4 liter beaker and with vigorous stirring add the following ingredients in the following order.

---

40 ml of ammonium hydroxide,
12 ml of Tween 80,
12 ml of L64,
15 grams of sodium bicarbonate,
15 grams of ammonium alginate (Superloid ® brand of Kelco Co.)

Add 700 ml of deionized or distilled water and when all of the ingredients have been thoroughly mixed, add 15 grams of sodium tetraborate dissolved in 150 ml of water. With continuous stirring, now slowly add 5 grams of calcium sulfate, 110 ml of glycerin, and stir for approximately ten minutes. Add 30 ml of dilute acetic acid, the addition of which and the preparation of which are as described in Example 1 above and then the composition may be layered onto a surface or onto a suitable backing, and dried, as described in Example 1 above.

EXAMPLE 3

The zinc salt of bacitracin, having a concentration of 67 IU/mg, is added in an amount of 230 mg to 10 ml of deionized water. Neomycin sulphate powder assaying as 704 mcg neomycin/mg of antibiotic is added to 10 ml of deionized water in an amount of 135 mg. Polymyxin B sulphate containing 8547 units of polymyxin B/mg of powder is added to 10 ml of deionized water in an amount of 22.6 mg. The three separate solutions are stirred until all of the antibiotics have been dissolved.

Antibiotic solutions thus prepared are added to 1200 ml of the 2.5% solution of sodium alginate Kelco brand HV and with continuous and vigorous stirring, the rest of the ingredients as set forth in Example 1 and in the concentrations utilized in Example 1 are added to the alginate-antibiotic composition which may then be may be spread and dried as described in Example 1 above.

EXAMPLE 4

To 1200 ml of a 2.5% sodium alginate preparation prepared as in Example 1 above, add the following ingredients in the following order:

| |
|---|
| 15 grams of sodium bicarbonate |
| 75 ml of glycerin |
| 6.9 ml of the surface active agent L64 |
| 6.9 ml of the surface active agent Tween 80 |

After stirring vigorously for approximately 10 minutes to ensure that all of the ingredients have been dispersed, add 150 ml of deionized water containing 50 grams of sodium tetraborate. After stirring for a few minutes to ensure that the borate solution has been thoroughly dispersed, add 60 ml of ammonium hydroxide and 75 ml of glycerin.

While continuously stirring, slowly add 1 gram of calcium sulfate into the vortex of the solution and then follow with 20 ml of a dilute solution of acetic acid prepared by diluting one part of glacial acetic acid with 2 parts of deionized water.

The diluted acetic acid should be added very slowly with a pipette, again into the vortex of the stirred mixture, and vigorous stirring continued for approximately five minutes.

Following the addition of the acetic acid, the composition will gradually become more viscous; one should continue to add 1000 ml of deionized water. With stirring continued, add 1 gram of a highly hydrophilic preparation called "Drimop"® as manufactured by Multisorb Technologies which is a sodium polyacrylate polymer.

The sodium polyacrylate polymer is highly hydrophilic and therefore, an amount of water would be retained by this product, even after drying in accord with the process set forth in Example 1. The unique value of adding a small amount of a highly hydrophilic preparation results in the retention of bound water to such a hydrophilic agent as the sodium polyacrylate polymer which thus results in a dressing having an amount of moisture which retains a 'cool' touch when the dressing is applied to an open wound. The "Drimop," sodium polyacrylate polymer being highly hydrophilic, also enhances the moisture-absorbing capacity of the dressing when it is applied to an open and/or exudating wound.

The alginate composition thus prepared may be spread on a flat surface and/or onto a suitable backing as described in Example 1 above and air- or oven-dried, again as described in Example 1.

EXAMPLE 5

An alginate foam composition is prepared as described in Example 1 above. The alginate may then be sterilized in a suitable container by ionizing or other suitable sterilizing radiation.

Using established aseptic techniques, a cell suspension is prepared from a culture of human, animal, or microbial cells and are aseptically harvested into a suitable buffered medium.

The cells thus suspended in a medium are then added aseptically to the sterile alginate foam slurry, as prepared above, with slow mixing.

The cell containing alginate foam slurry can then aseptically be layered onto a sterile sheet so that when dried, may be cut into appropriate sizes as required.

EXAMPLE 6

A 600 ml quantity of 2.5% sodium alginate as prepared above in Example 1 is added to a 4 liter container, and to the alginate is added the following ingredients in the following order:

| |
|---|
| 60 ml of glycerin |
| 200 ml of deionized water |
| 6 ml of Tween 80 |
| 6 ml of L64 surface active agent |
| 8 grams of sodium bicarbonate |
| 7.5 grams of ammonium alginate (as sold under the trade name of Superloid ® manufactured by Kelco Corporation) |

With continued and vigorous stirring, add 1.0 gram of calcium sulphate, and 50 grams of maltodextrin with a dextrose equivalent of 13.0 to 17.0 as prepared by Aldrich Chemical Company, Inc.

The ingredients are stirred vigorously with a stirrer until the composition becomes viscous and to this composition is added 20 ml of ammonium hydroxide and 150 ml of deionized water.

Dilute acetic acid prepared as described above in Example 1, is slowly added with a pipette to a total amount of 11.0 ml. The dilute acetic acid will react with the sodium bicarbonate and form a foam which remains intact in the semi-solid composition which can be continuously stirred until it is ready to pour onto the surface of a plate where it can be dried at room temperature or in an oven as described in Example 1.

Alternatively, the composition can be layered onto a gauze, cotton, or polyester backing where, when dry, it will adhere to and become affixed to the fibers of the backing.

The dried finished dressing can be cut, packaged into suitable packages as is well known in the profession and sterilized and stored in hospital settings to be used when required.

The alginate component in contact with an open wound will gradually become hydrocolloidal, will permit the continuous diffusion of the maltodextrin to the site of the wound, and will retain all of the clinical advantages that are delineated in U.S. Pat. Nos. 5,177,065 and 4,778,679 as well as in the literature of DeRoyal for its Multidex brand of maltodextrin wound dressing.

EXAMPLE 7

The ingredients that are described in Example 6 above are prepared in the same way and to the semi-solid composition is added 0.5 grams of ascorbic acid, to provide the beneficial effect of ascorbic acid as it is described in the U.S. Pat. Nos. 5,177,065 and 4,778,679 and in the literature of DeRoyal for its Multidex brand of maltodextrin wound dressing.

EXAMPLE 8

The alginate composition as described in Example 1, is prepared with stirring and to this alginate composition is added a dispersion of 10.0 ml of bovine collagen.

This composition can now be dried and layered with or without a backing as described in Example 1.

The above descriptions and examples illustrate particular constructions including the preferred embodiments of the solutions. However, the invention is not limited to the precise constructions described herein, but, rather, all modifications and improvements thereof encompassed within the scope of the invention.

The sodium alginate principally utilized in the examples described herein was one having an aqueous viscosity of 753 cP at 1.25% concentration. It is clear that other sodium alginates having other viscosities may be utilized without deviating from the novelty of the revelations contained in this patent as long as the alginate is of a concentration and viscosity that can be reasonably poured into a mold when a calcium or other anion alginate precipitating molecule is added to the sodium alginate.

Although the alginate used in the examples described herein was sodium alginate, it is clear that other water soluble alginates may be utilized without deviating from the novelty of the invention described herein such as water soluble ammonium alginate, magnesium alginate, or potassium alginate.

It is well known in the profession that various glycols will act as plasticizers and may be used to improve the flexibility of alginate films or fibers. The plasticizer that we have principally used in the examples described herein has been glycerin because of its low cost and ready availability. It is clear however that other plasticizers may be utilized such as propylene glycol or ethylene glycol without deviating from the novelty of the invention described herein.

In the examples cited herein, calcium chloride and calcium sulphate have been utilized to provide the calcium ion which precipitates the insoluble calcium alginate which serves to entrap into the calcium alginate matrix other components as described herein. It is clear, as has been mentioned, that other salts may be utilized to precipitate the alginate such as those of aluminum, zinc, copper, chromium, or silver and these insoluble alginates may readily be utilized to precipitate the coercive alginate mixtures described in the Examples provided herein without deviating from the essential merits of this invention. However, since the alginate compositions are to be utilized in and on biological tissues, the particular salt utilized to precipitate the alginate should be dictated by any restraints of toxicity or other untoward reactions that might result from their use for the preparation of bandages, dressings, or surgical products as herein described.

Note that in Example 8, we utilized bovine collagen as a component in the alginate mixture so that the insoluble calcium alginate gel will contain an agent which has hemostatic activity, and therefore would serve to stem the flow of blood from a wound when a dressing containing collagen is placed thereon. However, it is clear that other collagens such as porcine collagen may be incorporated into the alginate composition without deviating from the essential merits of this invention.

Note that in Example 3 we incorporate antibiotics into the alginate composition. Other medicinal agents which may be desirable in the treatment of wounds such as anti-inflammatory agents or antibacterial agents, can be incorporated into the alginate mixture without deviating from the novelty of the invention described herein.

Many of the examples described herein utilize the surface active agents such as those characterized as Tween 80 or Pluronic L64. These surface-active agents are utilized primarily to effect a dispersion between the aqueous and non-aqueous miscible components as well as to achieve a homogeneity with the component agents that are contained in the insoluble alginate compositions.

These surface active agents are also utilized in order to improve the wetting of a medical dressing or bandage in the event that a wound may be exudating, and the enhanced wicking in such a bandage or medical dressing serves to quickly absorb any blood or serum from a wound into th dressing. Other surface active agents, such as the Na salt of dodecyl $SO_4$ (sodium lauryl sulfate) or a member of the group of Tweens: Tween 20, polyoxyethylene sorbitan monolaurate; Tween 40, polyoxyethylene sorbitan monopalmitate; or Tween 85, polyoxyethylene sorbitan trioleate may be incorporated into the alginate composition without deviating from the novelty of the invention described herein.

Note that in the examples cited herein, the effervescent compound that reacts with the water soluble dilute acetic acid with the resultant evolution of a gas which become entrapped in the formation of the gel foam network is sodium bicarbonate. Other water soluble effervescent compounds may be utilized and other acids may be utilized to produce the evolution of gases which become entrapped in the alginate gel network without deviating from the novelty of the invention described herein. Thus, various water insoluble metal salts that can react with water soluble acids are calcium carbonate, calcium phosphate dibasic, barium carbonate, or zinc carbonate. Examples of suitable acids would include acetic acid, lactic acid, maleic acid, gluconic acid, and ascorbic acids.

Should it be desirable to utilize gases other than carbon dioxide to form the foam that forms the stable hydrogel composition described herein, inert gases such as nitrogen or argon, or other gases may be directly introduced into the alginate composition described in the claims herein as long as the alginate compositions described have a viscosity greater than the buoyancy of the gases entrapped therein. The addition of such other gases will cause the formation of stable hydrogel alginate foam compositions in accord with the novelty of the invention described herein.

Note that in Example 4, we introduce a highly hydrophilic chemical called "DriMop" (sodium polyacrylate polymer)

for the purpose of enhancing the moisture-absorbing capacity of the dressing. Other hydrophilic compounds may be utilized in order to achieve an enhanced moisture absorption of the dressing without deviating from the novelty of the invention described herein.

Example 6 described h rein incorporates a maltodextrin chemical within the alginate foam composition having a dextrose equivalent of 13.0–17.0. It is clear that other maltodextrins having dextrose equivalents other than 13.0–17.0 such as those which are available having dextrose equivalents of 4.0–7.0 and 16.5–19.5, may be utilized within the scope of the invention described herein without deviating from the novelty of the invention herein described.

The above descriptions and examples illustrate particular constructions including the preferred embodiments of the solutions. However, the invention is not limited to the precise constructions described herein, but, rather, all modifications and improvements thereof encompassed within the scope of the invention.

I claim:

1. A process for making a water-insoluble alginate sponge or foam product to be utilized in the preparation of wound dressings or surgical products comprising the steps of:
   (I) making an aqueous solution of a water-soluble alginate composition;
   (II) while allowing the total composition of (I) to be mixed, adding a di- or trivalent cation metal ion salt capable of complexing the water-soluble alginate to form a water-insoluble alginate hydrogel;
   (III) adding to the mixture of (II), a plasticizer, a surface active agent, sodium tetraborate, ammonium hydroxide, and a suitable medicinal agent;
   (IV) while continuing to mix the entire composition (III), adding an effervescent compound capable of effervescense upon reaction with a water-soluble acid;
   (V) adding to the composition (IV) a water-soluble acid;
   (VI) pouring said composite mixture of (V) onto a fibrous cloth contained in or on a tray, which fibrous cloth will become affixed to the alginate composition after the aqueous component of said composite mixture has evaporated.

2. The process of claim 1 wherein the effervescent compound is selected from a group consisting of the alkali metal carbonates.

3. The process of claim 2 wherein said effervescent compound is sodium carbonate.

4. The process of claim 1 wherein said effervescent compound is sodium bicarbonate.

5. The process of claim 1 wherein said water soluble acid is selected from the group consisting of acetic, lactic, malic, gluconic, hydrochloric, and ascorbic acids.

6. The process of claim 1 in which the fibrous cloth is selected from cloths prepared from cotton, polyester, wool, nylon, rayon or mixtures thereof.

7. The process of claim 1 wherein said water-soluble alginate is selected from a group consisting of ammonium, magnesium, potassium sodium salts of alginate, or mixtures thereof.

8. The process of claim 1 wherein said di- or trivalent cation is selected from a metal ion derived from salts selected from the group consisting of alkaline earth metal salts, alkali metal salts, transition metal salts, and mixtures thereof.

9. The process of claim 1 wherein said metal cation is selected from the group consisting of calcium, barium, copper, magnesium, iron, zinc, aluminum, manganese silver, strontium, and mixtures thereof.

10. The process of claim 1 wherein said medicament is selected from the group consisting of collagen, maltodextrin, antibiotics, antibacterial agents, an inflammatory agents, ascorbic acid, amino acids, and mixtures thereof.

11. The process of claim 1 wherein said plasticizer is selected from a group consisting of glycerin, propylene glycol, ethylene glycol, and polyethylene glycol or mixtures thereof.

12. The process of claim 1 wherein said surface active agent is selected from a group consisting of polyoxyethylene sorbitan monolaurate, polyoxyethylene sorbitan monopalmitate polyoxyethylene sorbitan monooleate, polyoxyethylene sorbitan trioleate, polyoxyethylene-polyoxypropylene block polymer, or a mixture thereof.

13. The process of claim 1 wherein the di- or trivalent cation metal salt complexing the water soluble alginate is calcium sulphate.

14. The process of claim 1 where in the di- or trivalent cation metal salt complexing the water-soluble alginate is calcium chloride.

15. The process of claim 1 in which the composition of (V) is sterilized.

16. The process of claim 15 in which the medicinal agent is a suspension of viable cells added to the sterilized composite mixture.

17. The process of claim 16 in which the composite mixture is poured onto a fibrous cloth contained in or on a tray, which fibrous cloth will become affixed to the alginate composition after the aqueous component of said composite mixture has evaporated.

18. The process of claim 16 in which the viable cells are mast cells.

19. The composition of claim 16 in which the viable cells are skin tissue cells.

20. The process of claim 19 wherein the effervescent compound is selected from a group consisting of the alkali metal carbonates.

21. The process of claim 20 wherein said effervescent compound is sodium carbonate.

22. The process of claim 16 wherein said effervescent compound is sodium bicarbonate.

23. The process of 16 wherein said water soluble acid is selected from the group consisting of acetic, lactic, malic, gluconic, hydrochloric, and ascorbic acids.

24. The process of claim 17 in which the fibrous cloth is selected from cloths prepared from cotton, polyester, wool, nylon, rayon, or mixtures thereof.

25. The process of claim 16 wherein said water-soluble alginate is selected from a group consisting of ammonium, magnesium, potassium, sodium salts of alginate, or mixtures thereof.

26. The process of claim 16 wherein said di- or trivalent cation is selected from a metal ion derived from salts selected from the group consisting of alkaline earth metal salts, alkali metal salts, transition metal salts, and mixtures thereof.

27. The process of claim 16 wherein said metal caution is selected from the group consisting of calcium, barium, copper, magnesium, iron, zinc, aluminum, manganese, silver, strontium, and mixtures thereof.

28. The process of claim 16 wherein said medicament is selected from the group consisting of collagen, maltodextrin, antibiotics, antibacterial agents, anti-inflammatory agents, ascorbic acid, amino acids, and mixtures thereof.

29. The process of claim 16 wherein said plasticizer is selected from a group consisting of glycerin, propylene glycol, ethylene glycol, and polyethylene glycol or mixtures thereof.

30. The process of claim 16 wherein said surface active agent is selected from a group consisting of polyoxethylene sorbitan monolaurate, polyoxethylene sorbitan monopalmitate, polyoxethylene sorbitan monooleate, polyoxyethylene sorbitan trioleate, polyoxethylene-polyoxypropylene block polymer, or a mixture thereof.

31. The process of claim 16 where in the di- or trivalent caution metal salt complexing the water soluble alginate is calcium sulphate.

32. The process of claim 16 wherein the di- or trivalent cation metal salt complexing the water soluble alginate is calcium chloride.

33. The process of claim 16 wherein the di- or trivalent cation metal salt complexing the water soluble alginate is calcium acetate.

* * * * *